United States Patent [19]

Abe

[11] Patent Number: 4,478,943
[45] Date of Patent: Oct. 23, 1984

[54] METHOD FOR MEASURING SILVER ION CONCENTRATION IN A SOLUTION

[75] Inventor: Akira Abe, Tokyo, Japan

[73] Assignee: Fuji Photo Film Co., Ltd., Kanagawa, Japan

[21] Appl. No.: 345,841

[22] Filed: Feb. 4, 1982

[30] Foreign Application Priority Data

Feb. 4, 1981 [JP] Japan ................................. 56-15388

[51] Int. Cl.$^3$ ............................................. G01N 21/00
[52] U.S. Cl. ................................................ 436/80
[58] Field of Search ...................... 436/80, 119, 164; 430/30

[56] References Cited

FOREIGN PATENT DOCUMENTS 2096766  1/1982  United Kingdom .................. 436/80

OTHER PUBLICATIONS

Mason Photographic Processing Chemistry Focal Press N.Y. 1975.

*Primary Examiner*—Hiram H. Bernstein
*Attorney, Agent, or Firm*—Sughrue, Mion, Zinn, Macpeak & Seas

[57] ABSTRACT

A method for measuring the silver concentration of a thiosulfate ion-containing solution is described, comprising providing for hypohalogenite ion to exist in an alkalized solution containing both silver ion and thiosulfate ion, and turbidometrically measuring the concentration of the slightly soluble silver salt thus-formed.

3 Claims, 1 Drawing Figure

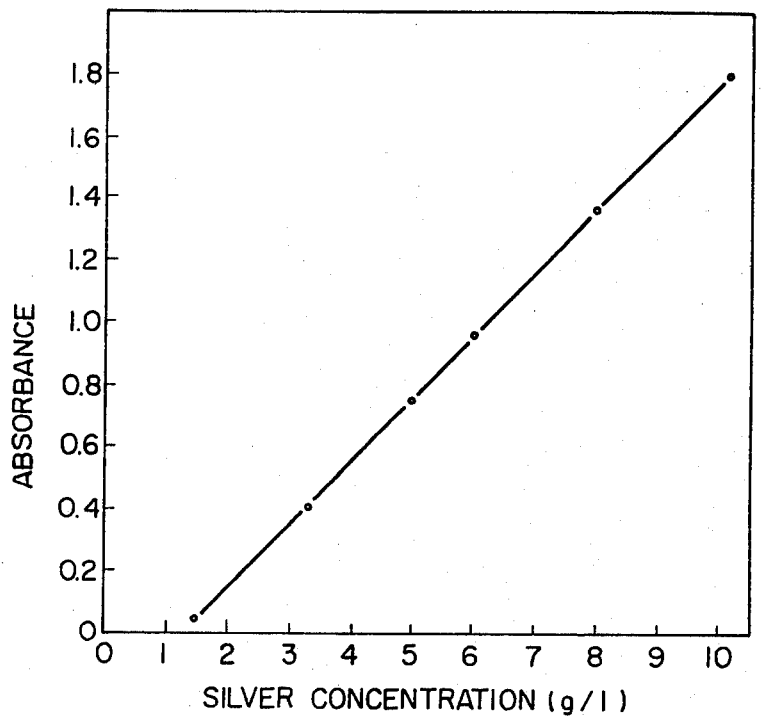

METHOD FOR MEASURING SILVER ION CONCENTRATION IN A SOLUTION

FIELD OF THE INVENTION

This invention relates to a method for measuring the silver ion concentration in a solution, and more particularly to a method for measuring the silver ion concentration of a solution in the copresence of a thiosulfate such as a fixing solution or a bleach-fixing solution used for processing silver salt light-sensitive materials.

From the viewpoint of measuring methods, this invention relates to turbidimetry which comprises adding a reagent capable of forming a slightly soluble salt with silver, and measuring turbidity due to the thus-produced slightly soluble compound by optical means.

BACKGROUND OF THE INVENTION

The general methods for measuring silver ion concentration include: (1) an absorptiometric method using dithizone, p-dimethylaminobenzylidene rhodanine, diethyl dithiocarbamate, tetraethylthiuram disulfide, 1,10-phenanthroline, thio-Michler's ketone, or the like (Mohamed, T. et al., *Analytical Chemistry*, Vol. 40, pp. 1986–1990 (1968)); (2) an ion electrode method (*Horiba Ion Electrode*, p. 33, published by Horiba Co., Ltd., 1979); (3) a precipitate-weighing method comprising forming a silver chloride precipitate and weighing the precipitate after drying; (4) a method of titrating with a thiocyanate solution; (5) a method of weighing silver electrodeposited on a cathode by electrolysis; (6) an atomic absorptiometric method; (7) a silver chloride turbidimetric method of producing silver chloride and optically measuring the turbidity (*Bunseki Kagaku Binran*, p. 384 (1961) by Maruzen Co., Ltd.; American Society of Testing Materials, *Methods of Chemical Analysis of Metals* (1960)); (8) a silver sulfide turbidimetric method of producing silver sulfide and optically measuring the turbidity (manual for a silver densitometer for fixing solution, viz., *Hi-Speed Model-2, Silver Test Meter*, sold by ARTISAN industries, Inc., U.S.A.); and (9) a filter paper method of dipping a cadmium sulfide-containing filter paper in a solution and optically measuring the change in color of the filter paper (*A New Way To Use Kodak Silver Estimating Test Papers*, published by Eastman Kodak Co., 1978).

Of the above-described methods, the absorptiometric method, ion electrode method, precipitate-weighing method, titration method, and silver chloride turbidimetric method are methods of measuring silver dissolved as $Ag^+$ (that is, as simple silver ions). Therefore, they cannot be applied to a system containing thiosulfate in a large amount, in which silver forms a complex ($Ag(S_2O_3)_2^{3-}$ or $Ag(S_2O_3)_3^{5-}$) together with thiosulfate ion. Also, the electrolytic weighing method cannot be applied, either, because silver recovered by electrolysis from a solution containing a large amount of coexisting materials such as a fixing solution contains impurities to such an extent that only inaccurate data are obtained. The atomic absorptiometric method is a method commonly used for analysis of metals, the principle of which is described in A. Walsh, *Spectrochem. Acta.*, Vol. 7, p. 108 (1955) in detail. The characteristics of this method are to provide accurate data speedily. Many informations on analysis of silver by this method are described in L. G. Hickey, *Spectrochem. Acta.*, Vol. 41, p. 546 (1968), W. Slavin, *Atomic Absorption Newsletter*, Vol. 3, p. 1 (1964), N. Kunimine, *Japan Analyst*, Vol. 16, No. 3, p. 185 (1967). However, this method requires expensive apparatus and cannot apply to the solution containing silver in an amount of more than 50 ml/l without dilution thereof. The method of separating silver sulfide followed by titration requires high skill.

The silver sulfide turbidimetric method is a method which comprises adding a water-soluble sulfide (usually a sodium sulfide solution) to a fixing solution, detecting the turbidity of resulting silver sulfide-containing solution by optical means (viz., by measuring transmission of absorbance using a colorimeter or a turbidimeter), and determining the silver concentration of a sample solution using a calibration curve previously made based on the correlation between transmission or light absorbance and silver concentration.

The defect of this method is that it cannot provide very accurate data, because there are so many materials in the system which produce slightly soluble salts with a sulfide. In addition, there are no effective masking means for preventing formation of other slightly soluble compounds than the silver compound.

There are many bleach-fixing solutions containing an iron (III) ethylenediaminetetraacetate chelate which have a bleaching action as well. Also, some bleaching solutions contain iron (III) salts such as ferric chloride, and such solutions are often followed by fixing solutions in photographic processing. In such cases, iron salts introduced from the preceding bleaching solution as deposits on light-sensitive materials often exist in the fixing solution in a considerable concentration. In addition, zinc, aluminum, etc., are often contained as well. In the silver sulfide turbidimetric method, not only silver, but also iron and zinc form sulfide particles and, in some cases, aluminum forms a labile sulfide to give a precipitate or cause coloration. Thus, light transmission or absorption is influenced so much by such copresent metals as well as the silver compound that very accurate silver concentration determinations cannot usually be obtained. In addition, it is known that silver sulfide does not have a definite composition, and that, when the sulfide ion concentration is high, there results reddish polysulfide (*Kagaku Dai Jiten*, Vol. 9, p. 653, Kyoritsu Shuppan). Therefore, growth of silver sulfide particles is so slow and complicated that there cannot be obtained stable absorbance (or transmission) with good reproducibility; thus, accurate silver concentration determinations very often cannot be obtained.

The filter paper method has the defect that it provides seriously varied data depending upon the state of the filter paper surface, degree of wetness after dipping the filter paper in a sample solution, filter paper-dipping time, time between withdrawing the filter paper from the solution and the measurement, and measuring temperature, with an inherent error of ±15% or more.

SUMMARY OF THE INVENTION

An object of the present invention is to provide a method for measuring the silver concentration both as free and complexed with thiosulfate in a solution containing both thiosulfate and silver thiosulfate complex ion, which is:

(1) simple in practice;
(2) speedy and accurate;
(3) needs no expensive apparatus; and
(4) is applicable to any fixing solution.

This object has been attained by providing for a hypohalogenite to exist in an alkalized solution containing both silver ion and thiosulfate ion, and turbidometrically measuring the concentration of the resulting slightly soluble silver salt.

BRIEF DESCRIPTION OF THE DRAWING

The FIGURE is a graph of the calibration curve prepared in Example 3, showing the relationship of absorbance and silver concentration.

DETAILED DESCRIPTION OF THE INVENTION

The present invention can be explained in more detail as follows, for example, in a case where sodium hypochlorite is used, being a representative hypohalogenite.

When sodium hypochlorite is added to a solution containing both silver ion and thiosulfate ion, the oxidation proceeds as follows.

$$Na_2S_2O_3 + 4NaOCl + H_2O \rightarrow Na_2SO_4 + H_2SO_4 + 4NaCl \tag{1}$$

NaCl thus-produced and remained NaOCl each react with silver to form silver chloride as follows.

$$NaCl + Ag^+ \rightarrow AgCl + Na^+ \tag{2}$$

$$3NaOCl + Ag^+ \rightarrow 2AgCl + NaClO_3 + 2Na^+ \tag{3}$$

Because thiosulfate is oxidized to form sulfuric acid and sulfate according to the reaction represented by formula (1), thiosulfate loses its silver chloride-dissolving ability, and in consequence, silver chloride formed according to the reaction represented by formulae (2) and (3) is deposited as its fine particles without dissolved with thiosulfate. The turbidity of the solution due to the deposition of silver chloride particles is measured by an optical means and thereby the concentration of silver in the solution is determined.

In a case where sodium hypobromite is used as sodium hypohalogenite, the silver salt thus-deposited is silver bromide, and in a case where sodium hypoiodite is used as sodium hypohalogenite, the silver salt thus-deposited is silver iodide. The turbidity of the solution due to the deposition of such silver salts is measured by the same optical means as in the measurement of silver chloride and thereby the concentration of silver in the solution is determined.

However, although even if only hypohalogenites are added to the solution containing both silver ion and thiosulfate ion, silver halide is deposited, the turbidity cannot be formed with good reproducibility and the quantitative correlation between the results of optical measurements and concentration of silver cannot be recognized.

As a result of extensive investigations, it is found that the turbidity is formed with a good reproducibility and with a good correlation quantitative to the concentration of silver in a case where the reactions represented by formulae (1) to (3) are performed, while keeping the pH of the solution at 7 or more by adding an alkali before addition of hypohalogenites to the solution, and the present invention is based on the above-mentioned findings.

The conventional silver sulfide turbidimetric method is conducted in a considerably strong acidic state, because the side reactions represented by the following formulae (4) and (5) in addition to silver halide-forming reaction represented by the formula (2) interfere with the quantitative correlation between transmission or light absorbance and silver concentration.

$$Ag^+ + OH^- \rightarrow AgOH \tag{4}$$

$$2Ag^+ + 2OH^- \rightarrow Ag_2O + H_2O \tag{5}$$

However, the present invention can obtain unexpected superiority by selecting an alkaline state which is quite different from in the conventional silver sulfide turbidimetric method.

Another aspect of the present invention is that not only oxidation of the thiosulfate occurs, but there is an increase in solution temperature due to the exothermic reaction of (1) which serves to rapidly produce silver chloride particles.

In addition, when alkalized, ammonia contained in the form of ammonium thiosulfate produces silver-ammine complex salt to increase the solubility of silver chloride, but the hypohalogenite oxidizes this ammonia to nitrogen, thus preventing production of the ammine complex salt.

The silver chloride turbidimetric method of the present invention is fundamentally different from the conventional silver chloride turbidimetric method in that the former is conducted in an alkaline state, whereas the latter in an acidic state.

Metals forming slightly soluble chlorides besides silver are only mercury (I) and thallium (I), and hence only silver selectively forms particles in a solution containing iron salts, zinc salts, and/or aluminum salts as well as silver.

Measurement of the turbidity due to the silver particles provides a linear relation between silver concentration and absorbance of a solution of any composition, with extremely slight variations.

In the reaction of the present invention, the silver concentration of a sample solution more desirably is determined for ranges of from 20 mg/l to 300 mg/l, and the hypohalogenite is desirably added to the solution so that its concentration falls within the range of from 0.07 mol/l to 0.6 mol/l.

As the chemicals for alkalizing the reaction solution, i.e., alkali agents, any known alkali agents can be used, with those having a buffering ability being preferable. Specific examples include phosphates of alkali metals (e.g., disodium phosphate, dipotassium phosphate, etc.), carbonates, borates, acetates, and hydroxides (e.g., sodium hydroxide and potassium hydroxide). These may be used in combinations of two or more thereof.

As the hypohalogenites, there can be used hypochlorite salts, hypobromites, and hypoiodites. Furthermore, chlorine gas, an aqueous bromine solution, and iodine may also be used in the present invention, since they produce hypohalogenites in an alkaline solution. Of these, hypochlorite salts are most preferable due to their stability. As the cations for the hypohalogenites, sodium ion and potassium ion are suitable.

The reaction between silver ion and hypohalogenite in a fixing solution proceeds well within three minutes. In the system of the present invention, the turbidity due to silver chloride particles is stable for about ten minutes, and must be measured within this period. The measuring light is not particularly limited as to wavelength. However, a bleach-fixing solution containing EDTA-Fe (III) chelate is colored, and therefore the turbidity of the solution is desirably measured using light of 600 nm or longer.

In the present invention, copresence of an alkali chloride (e.g., sodium chloride) upon reaction between hypochlorite and silver ion is advantageous, because the turbidity becomes rapidly stabilized thereby.

The present invention is most effective when applied to a thiosulfate-containing fixing solution or bleach-fixing solution used for the silver salt photographic processing.

The fixing solution may contain an organic sulfur compound whose fixing effect is known, or may contain a thiocyanate. Further, it may contain a water-soluble aluminum salt as a hardener. In this case, the pH of the solution is desirably adjusted to 9 or more to prevent formation of aluminum hydroxide.

As the method for measuring the concentration of the slightly soluble silver salt, it is simple and desirable to measure absorbance due to turbidity and determine the silver concentration using a previously prepared calibration curve. Other known measuring methods are of course employable.

The present invention will now be described in more detail by reference to examples of preferred embodiments of the present invention which, however, are not to be construed as limiting the invention.

EXAMPLE 1

Comparison of the Method of This Invention with Silver Sulfide Turbidimetric Method (1)

Method of this invention:
Solution I:
  Dipotassium phosphate: 70 g/l
  Potassium hydroxide: 10 g/l
Solution II: Commercially available sodium hypochlorite solution (containing 100 g/l of sodium hypochloride; made by Wako Junyaku Co., Ltd.)

Measuring procedure:
A 1 ml fixing solution sample was placed in a beaker, and 40 ml of solution I of the above formulation was added thereto. Subsequently, 10 ml of solution II of the above formulation was added thereto.

Silver sulfide turbidimetric method:
Solution A:
  Citric acid: 9 g/l
  Sodium citrate: 100 g/l
Solution B:
  Gelatin: 4 g/l
Solution C:
  Sodium sulfide (crystals): 100 g/l
  Sodium sulfite (anhydrous): 60 g/l
Measuring procedure:
A 1 ml fixing solution sample was placed in a beaker, and 5 ml of solution A and 5 ml of solution B of the above formulation were added thereto, followed by adding thereto 39 ml of water. Subsequently, 1 ml of solution C of the above formulation was added thereto.

The above-described procedures were conducted for fixing solutions for X-ray films (fixing solution F for Fuji X-ray film) containing ammonium thiosulfate, sodium sulfite, acetic acid, aluminum sulfate as well as 5 g/l of silver, and turbidity due to the slightly soluble silver compound produced was determined by measuring absorbance of the solutions for 670 nm light using a glass cell having a light-path length of 10 mm.

TABLE 1

| Sample Standing Time after Completion of Preparation Procedure | Absorbance (method of this invention) | Absorbance (silver sulfide turbidimetric method) |
|---|---|---|
| 1 min | 0.520 | 0.731 |
| 2 min | 0.721 | 0.807 |
| 3 min | 0.751 | 0.841 |
| 5 min | 0.756 | 0.900 |
| 10 min | 0.760 | 0.944 |
| 15 min | 0.752 | 0.967 |
| 30 min | 0.582 | 0.478 |

As is shown in Table 1, absorbance data obtained by the silver sulfide turbidimetric method significantly varied, whereas the method of the present invention provided stable absorbance data after about 3 minutes, which lasted for more than 10 minutes.

EXAMPLE 2

Comparison of the Method of This Invention with the Silver Sulfide Turbidimetric Method (2)

The two methods were compared with each other using fixing solutions listed in Table 2 in the same manner as in Example 1.

In Table 2, the fixing solution of Sample No. 1 is an exhausted fixing solution used for development of X-ray film, that of Sample No. 2 is an exhausted fixing solution used for development of color paper, and that of Sample No. 3 is an exhausted fixing solution used for development of 8 mm color reversal film. In both the method of the present invention and the method of silver sulfide turbidimetry, the solutions were permitted to stand for 3 minutes for the formation of slightly soluble silver salts.

TABLE 2

| No. | Sample | Ingredients | Silver* Concentration (g/l) | Absorbance (670 nm) *1 | *2 |
|---|---|---|---|---|---|
| 1 | Fixing solution for X-ray film | Ammonium thiosulfate 120 g/l Acetic acid 15 g/l Sodium sulfite 10 g/l Aluminum sulfate 10 g/l | 5.7 | 0.873 | 0.775 |
| 2 | Fixing solution for color paper | Ammonium thiosulfate 120 g/l Sodium sulfite 10 g/l EDTA-Fe (III) chelate 50 g/l | 5.5 | 0.837 | 1.187 |
| 3 | Fixing solution for 8 mm color reversal film | Sodium thiosulfate 120 g/l Sodium sulfite 10 g/l Citric acid-Fe (III) complex salt 5 g/l | 5.5 | 0.830 | 1.112 |

*Measured according to atomic absorptionmetric method using Atomic Absorption Flame Photometer (measurable wavelength: 3,280 Å) manufactured by Shimadzu Corp. as trademark of AA-610.
*1 Method of the present invention.
*2 Method of silver sulfide turbidimetry It was found that the silver sulfide turbidimetric method provided seriously varied absorbance data depending upon the copresent ingredients (particularly the copresence of iron salt), and thus failed to give accurate data regarding the silver concentration.

EXAMPLE 3

Solution I:
  Dipotassium phosphate: 70 g/l
  Potassium hydroxide: 10 g/l
Solution II: Commercially available sodium hypochlorite solution (containing 100 g/l sodium hypochlorite; made by Wako Junyaku Co., Ltd.)

Silver bromide was added, in a predetermined, stepwise increased amount, to a non-used fixing solution (Fixing Solution F for Fuji X-ray film) containing ammonium thiosulfate, sodium sulfite, acetic acid, and aluminum sulfate to prepare fixing solution samples containing predetermined, stepwise increased amounts of silver. 1 ml portion of each fixing sample was placed in a beaker, and 40 ml of solution I and 10 ml of solution II described above were added thereto, followed by stirring. After being allowed to stand for 3 minutes, it was placed in a glass cell having a light-path length of 10 mm, and absorbance for 670 nm light was measured using a spectrophotometer to prepare a calibration curve. The thus-obtained calibration curve is completely linear in the range of from 1.5 g/l to 10 g/l in silver concentration, as shown in FIG. 1.

Then, fixing solutions and bleach-fixing solutions as shown in Table 3 that had been used for development processing were used as samples. Absorbances of the samples were measured according to the foregoing methods, and silver concentrations were determined using the calibration curve.

Separately, the silver concentrations were measured according to the atomic absorptiometric method to compare the data with those obtained by the method of the present invention.

TABLE 3

| No. | Sample | Ingredients | Silver Concentration (g/l) *1 | *2 |
|---|---|---|---|---|
| 1 | Fixing solution for color paper | Ammonium thiosulfate 120 g/l EDTA-Fe (III) chelate 50 g/l Sodium sulfite 10 g/l | 9.1 | 9.1 |
| 2 | Fixing solution for color negative film | Ammonium thiosulfate 150 g/l Sodium thiosulfite 10 g/l | 6.1 | 6.0 |
| 3 | Fixing solution for lithographic film | Ammonium thiosulfate 120 g/l Acetic acid 15 g/l Sodium sulfite 10 g/l Aluminum sulfate 5 g/l | 4.6 | 4.7 |
| 4 | Fixing solution for 8 mm color reversal film | Sodium thiosulfate 120 g/l Sodium sulfite 10 g/l Citric acid-Fe (III) complex salt 5 g/l | 5.0 | 5.0 |
| 5 | Rinsing solution for bleach-fixed color paper | Ammonium thiosulfate 50 g/l EDTA-Fe (III) chelate 20 g/l Sodium sulfite 2 g/l | 1.8 | 1.7 |
| 6 | Fixing solution for X-ray film | Ammonium thiosulfate 120 g/l Acetic acid 15 g/l Sodium sulfite 10 g/l Aluminum sulfate 10 g/l | 3.8 | 3.8 |

*1 Method of the present invention
*2 Atomic absorptiometric method

As is shown above, the results almost completely coincided with each other as to a variety of fixing solutions and bleach-fixing solutions.

EXAMPLE 4

Solution I:
  Dipotassium phosphate: 70 g/l
  Potassium hydroxide: 10 g/l
Solution II: Commercially available aqueous bromine solution (containing 30 g/l bromine; made by Wako Junyaku Co., Ltd.)

Silver bromide was added, in a predetermined, stepwise increased amount, to a non-used fixing solution (Fixing Solution F for Fuji X-ray film) containing ammonium thiosulfate, sodium sulfite, acetic acid, and aluminum sulfate to prepare fixing solution samples containing predetermined, stepwise increased amounts of silver. 1 ml portion of each fixing sample was placed in a beaker, and 40 ml of solution I and 10 ml of solution II described above were added thereto, followed by stirring. After being allowed to stand for 3 minutes, it was placed in a glass cell having a light-path length of 10 mm, and absorbance for 670 nm light was measured using a spectrophotometer to prepare a calibration curve. The thus-obtained calibration curve is completely linear in the range of from 1.5 g/l to 10 g/l in silver concentration, which is analogous to that of Example 3.

Then, fixing solutions and bleach-fixing solutions as shown in Table 3 that had been used for development processing were used as samples. Absorbances of the samples were measured, and silver concentrations were determined using the calibration curve in the same manner as in Example 3.

Separately, the silver concentrations measured according to the atomic absorptiometric method in Example 3 were compared with those obtained by the method of the present invention.

TABLE 4

| No. | Sample | Silver Concentration (g/l) *1 | *2 |
|---|---|---|---|
| 1 | Fixing solution for color paper | 9.0 | 9.1 |
| 2 | Fixing solution for color negative film | 5.9 | 6.0 |
| 3 | Fixing solution for lithographic film | 4.7 | 4.7 |
| 4 | Fixing solution for 8 mm color reversal film | 4.9 | 5.0 |
| 5 | Rinsing solution for bleach-fixed color paper | 1.6 | 1.7 |
| 6 | Fixing solution for X-ray film | 3.7 | 3.8 |

*1 Method of the present invention
*2 Atomic absorptiometric method

As is shown above, the results almost completely coincided with each other as to a variety of fixing solutions and bleach-fixing solutions.

While the invention has been described in detail and with reference to specific embodiments thereof, it will be apparent to one skilled in the art that various changes and modifications can be made therein without departing from the spirit and scope thereof.

What is claimed is:

1. A method for measuring the silver concentration of a thiosulfate ion-containing solution, comprising providing for hypohalogenite ion to exist in an alkalized solution containing both silver ion and thiosulfate ion, and turbidometrically measuring the concentration of the slightly soluble silver salt thus-formed.

2. A method for measuring the silver concentration of a thiosulfate ion-containing solution as in claim 1, wherein the hypohalogenite ion is hypochlorite and the slightly soluble silver salt is sodium or potassium chloride.

3. A method for measuring the silver concentration of a thiosulfate ion-containing solution as in claim 1 or 2, wherein the concentration of the hypohalogenite is within the range of from 0.07 mol/l to 0.6 mol/l.

* * * * *